US 6,730,048 B1

United States Patent
Hare et al.

(10) Patent No.: US 6,730,048 B1
(45) Date of Patent: May 4, 2004

(54) APPARATUS AND METHOD FOR ULTRASONIC MEDICAL DEVICE WITH IMPROVED VISIBILITY IN IMAGING PROCEDURES

(75) Inventors: Bradley A. Hare, Chelmsford, MA (US); Janniah S. Prasad, Norwalk, CT (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 0 days.

(21) Appl. No.: 10/328,202

(22) Filed: Dec. 23, 2002

(51) Int. Cl.[7] ............................................... A61B 17/22
(52) U.S. Cl. ........................................ 601/2; 606/170
(58) Field of Search .................. 600/439; 601/2–4; 606/128, 159–169, 170, 171; 604/22

(56) References Cited

U.S. PATENT DOCUMENTS

| | | | | |
|---|---|---|---|---|
| 3,805,787 A | | 4/1974 | Banko | 128/276 |
| 3,991,929 A | | 11/1976 | Smith | 228/208 |
| 4,174,410 A | | 11/1979 | Smith | 427/57 |
| 4,571,520 A | | 2/1986 | Saito et al. | 310/327 |
| 4,870,953 A | * | 10/1989 | Don Micheal et al. | 606/128 |
| 4,920,954 A | * | 5/1990 | Alliger et al. | 606/128 |
| 4,922,902 A | | 5/1990 | Wuchinich et al. | 604/22 |
| 4,931,047 A | | 6/1990 | Broadwin et al. | 604/22 |
| 4,989,583 A | | 2/1991 | Hood | 128/24 A |
| 5,069,664 A | * | 12/1991 | Guess et al. | 604/22 |
| 5,112,300 A | | 5/1992 | Ureche | 604/22 |
| 5,180,363 A | | 1/1993 | Idemoto et al. | 202/32 |
| 5,269,297 A | * | 12/1993 | Weng et al. | 606/128 |
| 5,390,678 A | * | 2/1995 | Gesswein et al. | 606/1 |
| 5,449,369 A | * | 9/1995 | Imran | 606/159 |
| 5,540,656 A | * | 7/1996 | Pflueger et al. | 604/22 |
| 5,588,432 A | | 12/1996 | Crowley | 128/660.03 |
| 5,622,170 A | | 4/1997 | Schulz | 128/653.1 |
| 5,725,494 A | | 3/1998 | Brisken | 604/22 |
| 5,728,062 A | | 3/1998 | Brisken | 604/22 |
| 5,735,811 A | | 4/1998 | Brisken | 604/22 |
| 5,824,042 A | | 10/1998 | Lombardi et al. | 623/1 |
| 5,827,203 A | * | 10/1998 | Nita | 601/2 |
| 5,840,031 A | | 11/1998 | Crowley | 600/440 |
| 5,920,395 A | | 7/1999 | Schulz | 356/375 |
| 5,931,805 A | | 8/1999 | Brisken | 604/22 |
| 5,951,539 A | * | 9/1999 | Nita et al. | 604/526 |
| 5,971,949 A | * | 10/1999 | Levin et al. | 604/22 |
| 5,987,349 A | | 11/1999 | Schulz | 600/427 |
| 6,004,269 A | | 12/1999 | Crowley et al. | 600/439 |
| 6,007,514 A | * | 12/1999 | Nita | 604/22 |
| 6,010,498 A | | 1/2000 | Guglielmi | 606/32 |
| 6,203,568 B1 | | 3/2001 | Lombardi et al. | 623/1.13 |
| 6,277,084 B1 | * | 8/2001 | Abele et al. | 601/2 |
| 6,398,776 B1 | * | 6/2002 | Sekino et al. | 604/524 |
| 6,450,975 B1 | * | 9/2002 | Brennan et al. | 600/585 |

OTHER PUBLICATIONS

Sahagian, Richard, "Critical Insight: Marking Devices with Radiopaque Coatings," May 1999, *Medical Device & Diagnostic Industry Magazine* (http://www.devicelink.com/mddi/archive/99/05/011.html).

\* cited by examiner

*Primary Examiner*—Francis J. Jaworski
(74) *Attorney, Agent, or Firm*—Palmer & Dodge, LLP; Richard B. Smith; David J. Dykeman

(57) ABSTRACT

The present invention provides an apparatus and method for an ultrasonic medical device with improved visibility in imaging procedures. A medical device comprises an elongated probe having a material of high radiopacity at an at least one predetermined location of the probe wherein the material of high radiopacity is capable of withstanding series of vibrations of the elongated probe. The material of high radiopacity allows the elongated probe to be visualized in imaging procedures when the probe is inserted into a body. The present invention provides a method of improving the visibility of an ultrasonic medical device during a medical procedure by engaging a material of high radiopacity to a small diameter elongated probe wherein the material of high radiopacity engages the probe at an at least one predetermined location.

94 Claims, 6 Drawing Sheets

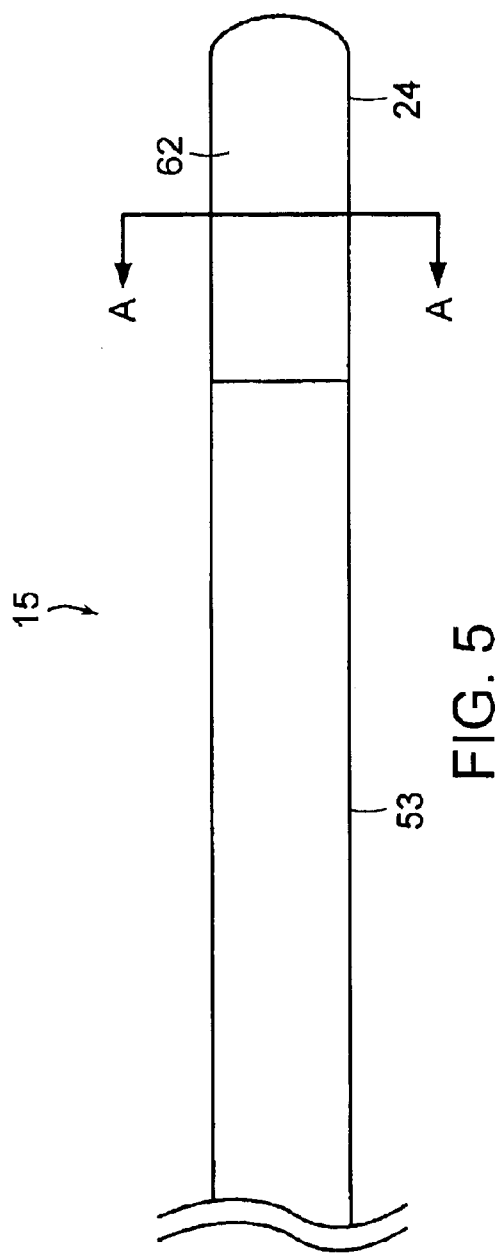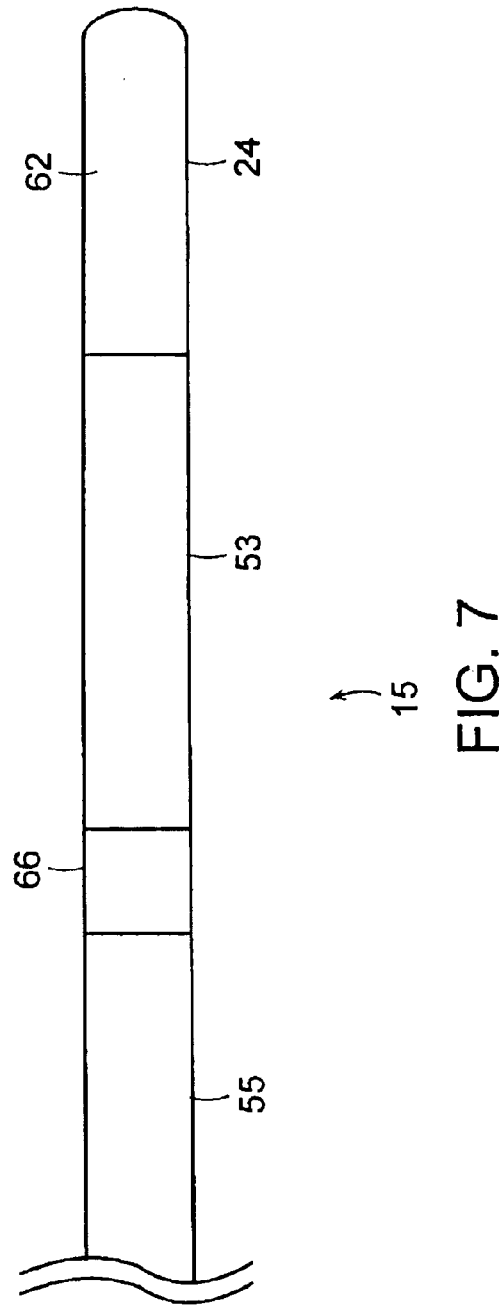

APPARATUS AND METHOD FOR ULTRASONIC MEDICAL DEVICE WITH IMPROVED VISIBILITY IN IMAGING PROCEDURES

RELATED APPLICATION(S)

None.

FIELD OF THE INVENTION

The present invention relates to an ultrasonic medical device, and more particularly to an apparatus and method for an ultrasonic medical device with improved visibility in imaging procedures for the detection inside of a body of an elongated probe comprising a material of high radiopacity;

BACKGROUND OF THE INVENTION

Vascular occlusive disease affects millions of individuals worldwide and is characterized by a dangerous blockage of blood vessels. Vascular occlusive disease includes thrombosed hemodialysis grafts, peripheral artery disease, deep vein thrombosis, coronary artery disease and stroke. Vascular occlusions (clots, intravascular blood clots or thrombus, occlusional deposits, such as calcium deposits, fatty deposits, atherosclerotic plaque, cholesterol buildup, fibrous material buildup, arterial stenoses) result in the restriction or blockage of blood flow in the vessels in which they occur. Occlusions result in oxygen deprivation ("ischemia") of tissues supplied by these blood vessels. Prolonged ischemia results in permanent damage of tissues which can lead to myocardial infarction, stroke, or death. Targets for occlusion include coronary arteries, peripheral arteries and other blood vessels. The disruption of an occlusion or thrombus can be affected by pharmacological agents and/or mechanical means. However, many thrombolytic drugs are associated with side effects such as severe bleeding which can result in a cerebral hemorrhage. Mechanical methods of treating thrombolysis include balloon angioplasty, which can result in ruptures in a blood vessel, and is generally limited to larger blood vessels. Scarring of vessels is common, which may lead to the formation of a secondary occlusion (a process known as restenosis). Another common problem is secondary vasoconstriction (classic recoil), a process by which spasms or an abrupt closure of the vessel occurs. These problems are common in treatments employing interventional devices. In traditional angioplasty, for instance, a balloon catheter is inserted into the occlusion, and through the application of hydraulic forces in the range of ten to fourteen atmospheres of pressure, the balloon is inflated. The non-compressible balloon applies this significant force to compress and flatten the occlusion, thereby opening the vessel for blood flow. However, these extreme forces result in the application of extreme stresses to the vessel, potentially rupturing the vessel, or weakening it thereby increasing the chance of post-operative aneurysm, or creating vasoconstrictive or restenotic conditions. In addition, the particulate matter is not removed, rather it is just compressed. Other mechanical devices that drill through and attempt to remove an occlusion have also been used, and create the same danger of physical damage to blood vessels.

Ultrasonic probes using ultrasonic energy to fragment body tissue have been used in many surgical procedures (see, e.g., U.S. Pat. No. 5,112,300; U.S. Pat. No. 5,180,363; U.S. Pat. No. 4,989,583; U.S. Pat. No. 4,931,047; U.S. Pat. No. 4,922,902; and U.S. Pat. No. 3,805,787). The use of ultrasonic energy has been proposed both to mechanically disrupt clots, and to enhance the intravascular delivery of drugs to clot formations (see, e.g., U.S. Pat. No. 5,725,494; U.S. Pat. No. 5,728,062; and U.S. Pat. No. 5,735,811). Ultrasonic devices used for vascular treatments typically comprise an extracorporeal transducer coupled to a solid metal wire which is then threaded through the blood vessel and placed in contact with the occlusion (see, e.g., U.S. Pat. No. 5,269,297). In some cases, the transducer, comprising a bendable plate, is delivered to the site of the clot (see, e.g., U.S. Pat. No. 5,931,805).

The ultrasonic energy produced by an elongated probe is in the form of very intense, high frequency sound vibrations that result in physical reactions in the water molecules within a body tissue or surrounding fluids in proximity to the probe. These reactions ultimately result in a process called "cavitation," which can be thought of as a form of cold (i.e., non-thermal) boiling of the water in the body tissue, such that microscopic bubbles are rapidly created and destroyed in the water creating cavities in their wake. As surrounding water molecules rush in to fill the cavity created by collapsed bubbles, they collide with each other with great force. Cavitation results in shock waves running outward from the collapsed bubbles which can wear away or destroy material such as surrounding tissue in the vicinity of the elongated probe.

Some ultrasonic devices include a mechanism for irrigating an area where the ultrasonic treatment is being performed (e.g., a body cavity or lumen) in order to wash tissue debris from the area of treatment. Mechanisms used for irrigation or aspiration described in the art are generally structured such that they increase the overall cross-sectional profile of the elongated probe, by including inner and outer concentric lumens within the probe to provide irrigation and aspiration channels. In addition to making the probe more invasive, prior art probes also maintain a strict orientation of the aspiration and the irrigation mechanism, such that the inner and outer lumens for irrigation and aspiration remain in a fixed position relative to one another, which is generally closely adjacent to the area of treatment. Thus, the irrigation lumen does not extend beyond the suction lumen (i.e., there is no movement of the lumens relative to one another) and any aspiration is limited to picking up fluid and/or tissue remnants within the defined area between the two lumens.

As discussed above, medical devices utilizing ultrasonic energy to destroy biological material in the human body are known in the art. A major drawback of existing ultrasonic devices comprising an elongated probe for biological material removal is that they are relatively slow in comparison to procedures that involve surgical excision. This is mainly attributed to the fact that such ultrasonic devices rely on imparting ultrasonic energy to contacting biological material by undergoing a longitudinal vibration of the probe tip, wherein the probe tip is mechanically vibrated at an ultrasonic frequency in a direction parallel to the probe longitudinal axis. This, in turn, produces a biological material destroying effect that is entirely localized at the probe tip, which substantially limits its ability to ablate large biological material areas in a short time. An ultrasonic medical device with a multiple material coaxial construction for conducting axial vibrations is known in the art (see, e.g., U.S. Pat. No. 6,277,084). In addition to prior art ultrasonic devices being slow, previous ultrasonic methods of treating plaque still include many undesirable complications and dangers.

The inability to detect the location of an ultrasonic probe during a medical procedure deep in a body has not been solved by the prior art. Prior art ultrasonic probes are typically comprised of a high capacitance material. Often, such high capacitance materials have a low radiopacity. Low radiopacity materials allow the passage of x-rays or other radiation. Because these high capacitance materials do not absorb enough radiation, a user is unable to locate the exact position of the ultrasonic probe inside the human body during a medical procedure which includes an imaging procedure.

Imaging procedures typically include fluoroscopy or radiography. Fluoroscopy is a method of viewing the interior of the body, which would be opaque to longer wavelength electromagnetic radiation, in which a continuous x-ray beam is passed through the body part being examined, and is transmitted to a television-like monitor so that the body part and its motion can be seen in detail. Fluoroscopy is used in many types of examinations and procedures, such as barium x-rays, cardiac catherization, and placement of intravenous (IV) catheters (hollow tubes into veins or arteries). Radiography is a procedure that uses standard x-rays to analyze the bony and soft tissue anatomy for diagnosis.

Prior art attempts to visualize materials in a human body during a medical procedure have been less than successful. For example, U.S. Pat. No. 5,824,042 to Lombardi et al. discloses an endoluminal prosthesis for deployment in a lumen of a patient's body, the prosthesis comprising a tubular fabric liner and a radially expandable frame supporting the liner. A plurality of imagable bodies are attached to the liner, the imagable bodies providing a sharp contrast so as to define a pattern which indicates the prosthesis position when the prosthesis is imaged within the patient body. Lombardi et al. requires the plurality of imagable bodies to be stitched into tubular fabric liner; the plurality of imagable bodies could not be stitched into an ultrasonic probe. The plurality of imagable bodies disclosed in Lombardi et al. would not be able to withstand vibrations of an ultrasonic device. Therefore, a need remains in the art for an apparatus and method of visualizing the position of an ultrasonic probe during a medical procedure which includes an imaging procedure.

U.S. Pat. No. 5,622,170 to Schulz discloses a system for sensing at least two points on an object for determining the position and orientation of the object relative to another object. Two light emitters mounted in spaced relation to each other on an external portion of an invasive probe, remaining outside an object into which an invasive tip is inserted, are sequentially strobed to emit light. In Schulz, a computer determines the position and orientation of the invasive portion of the probe inside the object by correlating the position of the invasive portion of the probe relative to a predetermined coordinate system with a model of the object defined relative to the predetermined coordinate system. Schulz does not allow for the position of the probe to be determined directly but rather provides a representation of the probe's position relative to a predetermined coordinate system. Also, Schulz discloses an expensive, complicated and complex method of approximating the position of a probe once inside a body. Therefore, a need remains in the art for an apparatus and method of visualizing the position of an ultrasonic probe during a medical procedure which includes an imaging procedure.

U.S. Pat. No. 5,588,432 to Crowley discloses an acoustic imaging system for use within a heart comprising a catheter, an ultrasound device incorporated into the catheter, and an electrode mounted on the catheter. In Crowley, a central processing unit creates a graphical representation of the internal structure, and superimposes items of data onto the graphical representation at locations that represent the respective plurality of locations within the internal structure corresponding to the plurality of items of data. Like Schulz, Crowley does not allow for the position of the medical device to be determined directly, but rather provides a representation of the device's position corresponding to the plurality of items of data. Therefore, a need remains in the art for an apparatus and a method of visualizing the position of an ultrasonic probe during a medical procedure which includes an imaging procedure.

Other attempts to improve the detection of a device used in a medical procedure that includes an imaging procedure include attaching a number of metal bands or the use of the device in conjunction with a barium-filled catheter. Although such devices may improve the ability to detect a material that is not easily visible, they are difficult to use in conjunction with an ultrasonic probe because the metal bands are difficult to attach to an ultrasonic probe and can separate from the ultrasonic probe due to vibration of the ultrasonic probe. A barium-filled catheter allows for improved detection of the catheter, but does not allow for the exact location of the ultrasonic probe to be determined. Also, barium-filled catheters are known in the art to obstruct the ability to view surrounding arteries and veins. Therefore, a need remains in the art for an apparatus and a method of better visualizing the position of an ultrasonic probe during a medical procedure that includes an imaging procedure.

Other attempts at improving the ability to detect a device inside the body include using a high-vacuum deposition process that results in a thin-film coating. Traditional ion-beam-assisted deposition (IBAD) employs an electron-beam evaporator to create a vapor of atoms that coats the surface of the device. A similar process known as microfusion comprises placing the substrate to be coated between two magnetrons. Provision is made for an adjustable bias to be applied to the substrate, as required, to control ion energy and flux. The prior art processes are complex, difficult to implement, and expensive. Therefore, a need remains in the art for a simple and inexpensive apparatus and a method of detecting the position of an ultrasonic probe during a medical procedure that includes an imaging procedure.

The prior art devices and methods of visualizing an ultrasonic probe inside a body are complex, complicated and expensive. Therefore, there is a need in the art for an apparatus and method for an ultrasonic medical device with improved visibility in imaging procedures that is simple, user-friendly, reliable and cost effective.

SUMMARY OF THE INVENTION

The present invention provides an apparatus and method for an ultrasonic medical device with improved visibility in imaging procedures. Imaging procedures include, but are not limited to, fluoroscopy, radiography, tomography, digital x-ray imaging, ultrasound and magnetic resonance imaging (MRI).

The present invention is a medical device comprising an elongated probe having a material of high radiopacity at an at least one predetermined location of the elongated probe wherein the material of high radiopacity is capable of withstanding a series of vibrations of the elongated probe. In a preferred embodiment of the present invention, the material of high radiopacity is at a distal end of the elongated probe and allows the elongated probe to be visualized in imaging procedures.

The present invention is an elongated probe comprising a material of low radiopacity and a material of high radiopacity that allows the medical device to benefit from the high capacitance properties of the material of low radiopacity and the ability of the material of high radiopacity to absorb radiation to allow the elongated probe to be visualized during a medical procedure which includes an imaging procedure. The material of high radiopacity is biocompatible and non-toxic and is selected from a group including, but not limited to, tantalum, tungsten, gold, molybdenum and alloys thereof.

The present invention is an apparatus comprising a small diameter elongated probe having a material of high radiopacity. The small diameter of the elongated probe allows for facile insertion of the elongated probe into a body. The material of high radiopacity allows for detection of the elongated probe when used inside a body during a medical procedure which includes an imaging procedure.

The present invention also provides a method of improving the visibility of an ultrasonic device during a medical procedure by engaging a material of high radiopacity to a small diameter elongated probe at an at least one predetermined location. The material of high radiopacity is engaged to the elongated probe by processes including, but not limited to, butt-welding, brazing, shrink fitting, lap welding, threaded fitting, twisting the materials or other mechanical or metallurgical connections.

The present invention is a medical device comprising an elongated probe having a material of high radiopacity at a plurality of locations of the elongated probe. The present invention provides an ultrasonic medical device with improved visibility in imaging procedures that is simple, user-friendly, reliable and cost effective.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 5 shows a fragmentary view of an alternative embodiment of the present invention wherein a cross section of a distal end of an elongated, ultrasonic probe has a material of high radiopacity and a material of low radiopacity.

FIG. 7 shows a fragmentary view of an alternative embodiment of the present invention wherein an elongated, ultrasonic probe has a composite cross section of a material of high radiopacity and a material of low radiopacity at a plurality of predetermined locations of the elongated, ultrasonic probe.

Figure 1:
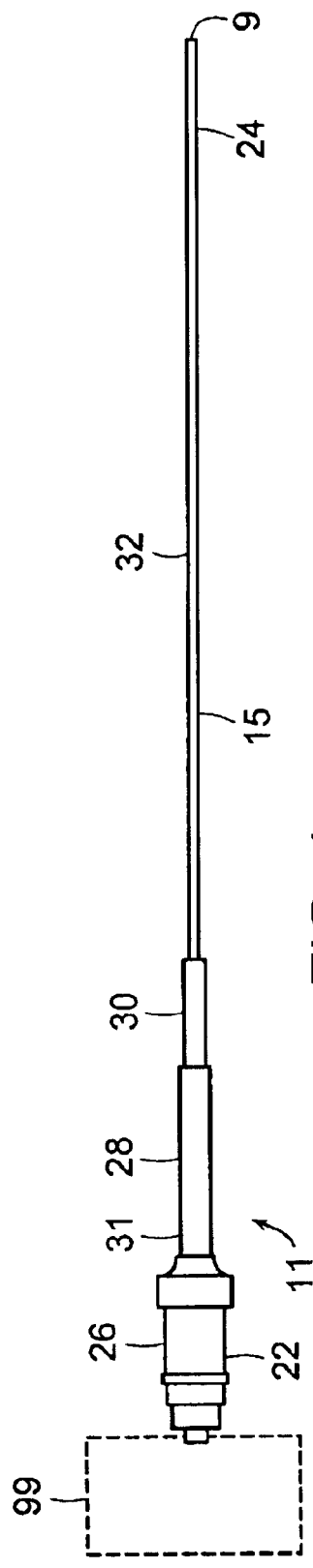
FIG. 1 shows a side plan view of an ultrasonic medical device of the present invention capable of operating in a transverse mode.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of the present invention.

DETAILED DESCRIPTION

The present invention provides an apparatus and a method for using a medical device comprising an elongated, ultrasonic probe with a material of high radiopacity in a medical procedure which includes an imaging procedure. The material of high radiopacity is capable of withstanding a series of vibrations of the elongated probe and allows the elongated probe to be visualized in imaging procedures including, but not limited to, fluoroscopy, conventional radiography, tomography, digital x-ray imaging, ultrasound, magnetic resonance imaging (MRI) and other image modalities. In a preferred embodiment of the present invention, the material of high radiopacity is at a distal end of the elongated probe. In another embodiment of the present invention, the material of high radiopacity is at a plurality of predetermined locations of the elongated probe.

The following terms and definitions are used herein:

"Ablate" as used herein refers to removing, clearing, destroying or taking away debris. "Ablation" as used herein refers to the removal, clearance, destruction, or taking away of debris.

"Cavitation" as used herein refers to shock waves produced by ultrasonic vibration, wherein the vibration creates a plurality of microscopic bubbles which rapidly collapse, resulting in a molecular collision by water molecules which collide with force thereby producing the shock waves.

"Low radiopacity" as used herein refers to a characteristic of a material that allows the passage of x-rays or other radiation, thereby resulting in a lesser degree of visibility in an imaging procedure than would be possible with a material of high radiopacity.

"High radiopacity" as used herein refers to a characteristic of a material that does not allow the passage of a substantial amount of x-rays or other radiation, thereby resulting in a higher degree of visibility in an imaging procedure than would be possible with a material of low radiopacity.

"Node" as used herein refers to a region of minimum energy emitted by an ultrasonic probe at or proximal to a specific location along the longitudinal axis of the probe.

"Anti-node" as used herein refers to a region of maximum energy emitted by an ultrasonic probe at or proximal to a specific location along the longitudinal axis of the probe.

"Probe" as used herein refers to a device capable of being adapted to an ultrasonic generator, which is capable of propagating the energy emitted by the ultrasonic generator along its length, resolving this energy into effective cavitational energy at a specific resonance (defined by a plurality of nodes and a plurality of anti-nodes along an "active area" of the probe) and is capable of acoustic impedance transformation of ultrasound energy to mechanical energy.

"Ultrasonic probe" as used herein refers to any medical device utilizing ultrasonic energy with the ability to ablate debris including, but not limited to, probes, elongated wires, and similar devices known to those skilled in the art.

"Transverse" as used herein refers to vibration of a probe not parallel to the longitudinal axis of the probe. A "transverse wave" as used herein is a wave propagated along an ultrasonic probe in which the direction of the disturbance at each point of the medium is not parallel to the wave vector.

"Biological material" as used herein refers to an aggregation of matter including, but not limited to, a group of similar cells, intravascular blood clots or thrombus, fibrin, calcified plaque, calcium deposits, occlusional deposits, atherosclerotic plaque, fatty deposits, adipose tissues, atherosclerotic cholesterol buildup, fibrous material buildup, arterial stenoses, minerals, high water content tissues, platelets, cellular debris, wastes and other occlusive materials.

An ultrasonic medical device operating in a transverse mode of the present invention is illustrated generally at 11 in FIG. 1. The ultrasonic medical device operating in a transverse mode includes an elongated probe 15 which is coupled to a device providing a source or a generator 99 (shown in phantom in FIG. 1) for the production of ultrasonic energy. In one embodiment of the present invention, the ultrasonic generator 99 is a physical part of the ultrasonic medical device 11. In another embodiment of the present invention, the ultrasonic generator 99 is not a physical part of the ultrasonic medical device 11. A transducer 22 transmits ultrasonic energy received from the generator 99 to the probe 15. Energy from the ultrasonic generator 99 is transmitted along the length of the probe 15, causing the probe 15 to vibrate in a transverse mode. The probe 15 includes a proximal end 31 and a distal end 24. The transducer 22 is capable of engaging the ultrasonic probe 15 at the proximal end 31 with sufficient restraint to form an acoustical mass that can propagate the ultrasonic energy provided by the ultrasonic generator 99. The distal end 24 of the probe 15 is a thin terminal interval ending in a probe tip 9. The probe tip 9 can be any shape including, but not limited to, bent, a ball or larger shapes for removing a larger area of biological material. The probe 15 is flexible and articulable so it can be inserted into a vasculature of the body. In a preferred embodiment of the present invention shown in FIG. 1, the cross section of the elongated probe 15 is approximately circular and the diameter of the probe 15 decreases in a gradual tapered manner at defined intervals 26, 28, 30, and 32. In other embodiments of the present invention, the shape of the cross section of the probe 15 includes, but is not limited to, square, trapezoidal, oval, triangular, circular with a flat spot and similar cross sections. Those skilled in the art will recognize that other cross sectional geometric configurations and diameters known in the art would be within the spirit and scope of the present invention.

A transverse mode of vibration of the elongated probe 15 according to the present invention differs from an axial (or longitudinal) mode of vibration disclosed in the prior art. Rather than vibrating in the axial direction, the probe 15 of the present invention vibrates in a direction transverse (not parallel) to the axial direction. As a consequence of the transverse vibration of the probe 15, the biological material-destroying effects of the device 11 are not limited to those regions of the probe tip 9 coming into contact with a biological material. Rather, as a length of the probe 15 is positioned in proximity to a diseased area or lesion, the biological material is removed in all areas adjacent to the multiplicity of energetic anti-nodes that are produced along the length of the flexible probe 15, typically in a region having a radius of up to about 6 mm around the probe 15.

Transversely vibrating ultrasonic probes for biological material ablation are described in the Assignee's co-pending patent applications (U.S. Ser. No. 09/776,015, U.S. Ser. No. 09/618,352 and U.S. Ser. No. 09/917,471) which further describe the design parameters for such a probe and its use in ultrasonic devices for ablation and the entirety of these applications are hereby incorporated herein by reference.

Figure 2A:
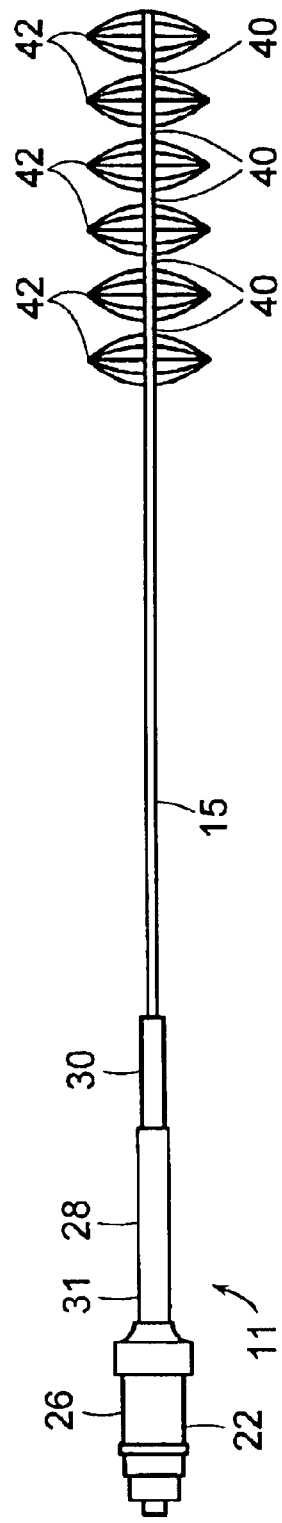
FIG. 2A shows a side plan view of an ultrasonic medical device operating in a transverse mode of the present invention showing a plurality of nodes and a plurality of anti-nodes along an active area of an elongated, ultrasonic probe.

Due to the probe 15 design, as the ultrasonic energy propagates along the length of the probe 15, the ultrasonic energy manifests as a series of transverse vibrations, rather than longitudinal vibrations. As shown in FIG. 2A, a plurality of nodes 40 occur along the length of the probe 15 at repeating intervals. The nodes 40 are areas of minimum energy and minimum vibration. A plurality of anti-nodes 42, or areas of maximum energy and maximum vibration, also occur at repeating intervals along the length of the probe 15. The number of nodes 40 and anti-nodes 42, and the spacing of the nodes 40 and anti-nodes 42 of the probe 15 depends on the frequency of the energy produced by the ultrasonic generator 99. The separation of the nodes 40 and the anti-nodes 42 is a function of the frequency, and can be affected by tuning the probe 15. In a properly tuned probe 15, the anti-nodes 42 will be found at a position exactly one-half of the distance between the nodes 40 located adjacent to each side of the anti-node 42. The effects of the ultrasonic medical device 11 operating in a transverse mode of the present invention for destroying biological material are not limited to those regions of the probe tip 9 coming into contact with a biological material. Rather, as the probe 15 is swept through an area of the biological material, preferably in a windshield-wiper fashion, the biological material is removed in all areas adjacent to the plurality of anti-nodes 42 being produced along a length of the probe 15. The extent of the cavitational energy produced by the probe 15 is such that the cavitational energy extends radially outward from the length of the probe 15 at the anti-nodes 42 along the length of the probe 15. In this way, actual treatment time using the transverse mode ultrasonic medical device 11 according to the present invention is greatly reduced as compared to methods disclosed in the prior art that primarily utilize longitudinal vibration (along the axis of the probe) for biological material ablation.

By eliminating the axial motion of the probe 15 and allowing transverse vibrations only, the active probe 15 can cause fragmentation of large areas of biological material spanning the entire length of the active portion of the probe 15 due to generation of multiple cavitational anti-nodes 42 along the length of the probe 15 not parallel to the axis of the probe 15. Since substantially larger affected areas can be denuded of the biological material in a short time, actual treatment time using the transverse mode ultrasonic medical device 11 according to the present invention is greatly reduced as compared to methods using prior art probes that primarily utilize longitudinal vibration (along the axis of the probe) for ablation. A distinguishing feature of the present invention is the ability to utilize probes of extremely small diameter compared to prior art probes, without loss of efficiency, because the biological material fragmentation process is not dependent on the area of the probe tip 9 (distal end). Highly flexible probes can therefore be designed to mimic device shapes that enable facile insertion into biological material spaces or extremely narrow interstices that contain biological material. Another advantage provided by the present invention is the ability to rapidly remove biological material from large areas within cylindrical or tubular surfaces.

A significant advantage of the present invention is that it physically destroys and removes biological material (especially adipose or other high water content tissue) through the mechanism of non-thermal cavitation. The removal of biological material by cavitation also provides the ability to remove large volumes of biological material with a small diameter probe, without making large holes in the tissue or the surrounding areas. The use of cavitation as the mechanism for destroying biological material, together with the use of irrigation and aspiration, allows the present invention to destroy and remove biological material within a range of temperatures of about ±7° C. from normal body temperature. Therefore, complications attendant with the use of thermal destruction or necrosis, such as swelling or edema, as well as loss of elasticity are avoided. Furthermore, the use of fluid irrigation can enhance the cavitation effect on surrounding biological material, thus speeding biological material removal.

The cavitation energy is the energy that is expelled from the probe 15 in a stream of bubbles which must contact the biological material to cause ablation. Therefore, blocking the cavitation bubble stream from contacting biological material will spare the biological material from ablation, while directing the cavitation bubble stream to contact the biological material will cause ablation.

The number of nodes 40 and anti-nodes 42 occurring along the axial length of the probe 15 is modulated by changing the frequency of energy supplied by the ultrasonic generator 99. The exact frequency, however, is not critical and the ultrasonic generator 99 run at, for example, about 20 kHz is generally sufficient to create an effective number of biological material destroying anti-nodes 42 along the axial length of the probe 15. Those skilled in the art understand it is possible to adjust the dimensions of the probe 15, including diameter, length, and distance to the ultrasonic energy generator 99, in order to affect the number and spacing of the nodes 40 and anti-nodes 42 along the length of the probe 15. The present invention allows the use of ultrasonic energy to be applied to biological material selectively, because the probe 15 conducts energy across a frequency range from about 20 kHz through about 80 kHz. The amount of ultrasonic energy to be applied to a particular treatment site is a function of the amplitude and frequency of vibration of the probe 15. In general, the amplitude or throw rate of the energy is in the range of about 25 microns to about 250 microns, and the frequency in the range of about 20,000 Hertz to about 80,000 Hertz (20 kHz–80 kHz). In a preferred embodiment of the present invention, the frequency of ultrasonic energy is from about 20,000 Hertz to about 35,000 Hertz (20 kHz–35 kHz). Frequencies in this range are specifically destructive of biological materials including, but not limited to, hydrated (water-laden) tissues such as endothelial tissues, while substantially ineffective toward high-collagen connective tissue, or other fibrous tissues including, but not limited to, vascular tissues, epidermal, or muscle tissues.

In a preferred embodiment of the present invention, the ultrasonic generator 99 is mechanically coupled to the proximal end 31 of the probe 15 to oscillate the probe 15 in a direction transverse to its longitudinal axis. In another embodiment of the present invention, a magneto-strictive generator may be used for generation of ultrasonic energy. The preferred generator is a piezoelectric transducer that is mechanically coupled to the probe 15 to enable transfer of ultrasonic excitation energy and cause the probe 15 to oscillate in a transverse direction relative to its longitudinal axis. The ultrasonic medical device 11 is designed to have a small cross-sectional profile, which also allows the probe 15 to flex along its length, thereby allowing the probe 15 to be used in a minimally invasive manner. Transverse oscillation of the probe 15 generates a plurality of cavitation anti-nodes 42 along the longitudinal axis of the probe 15, thereby efficiently destroying the biological materials that come into proximity with the energetic anti-nodes 42. A significant feature of the present invention resulting from the transversely generated energy is the retrograde movement of debris, e.g., away from the probe tip 9 and along the shaft of the probe 15.

The amount of cavitation energy to be applied to a particular site requiring treatment is a function of the amplitude and frequency of vibration of the probe 15, the longitudinal length of the probe 15, the proximity of the probe 15 to a biological material, and the degree to which the probe length is exposed to the biological material.

Figure 2B:
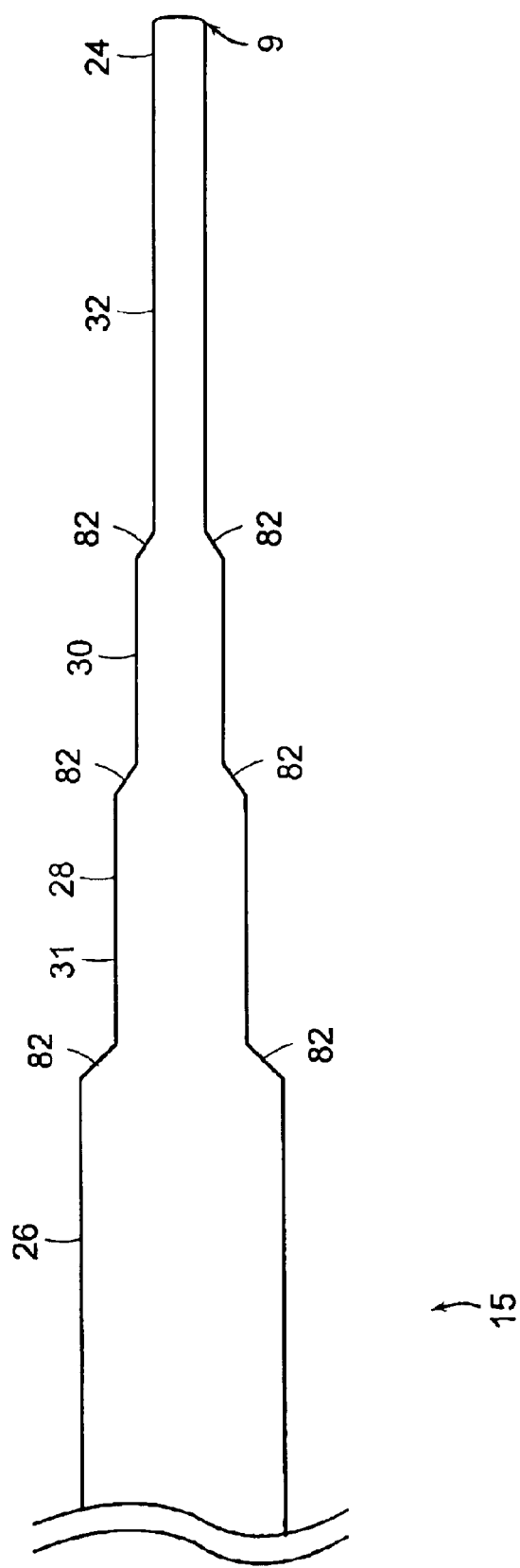
FIG. 2B shows a fragmentary side plan view of an elongated, ultrasonic probe of the present invention with a plurality of transitions.

FIG. 2B shows a fragmentary side plan view of an elongated, ultrasonic probe of the present invention with a plurality of transitions. The probe 15 comprises the distal end 24, the proximal end 31 and a length of probe between the distal end 24 and the proximal end 31. In an embodiment of the present invention, the diameter of the probe 15 gradually decreases from the proximal end 31 to the distal end 24.

In a preferred embodiment of the present invention, the elongated probe 15 has a small diameter. In an embodiment of the present invention, the diameter of the distal end 24 of the elongated probe 15 is about 0.006 inches. In another embodiment of the present invention, the diameter of the distal end 24 of the elongated probe 15 is about 0.015 inches. In other embodiments of the present invention, the diameter of the distal end 24 of the elongated probe 15 varies between about 0.003 inches and about 0.025 inches. Those skilled in the art will recognize an elongated probe 15 can have a diameter at the distal end 24 smaller than about 0.003 inches, larger than about 0.025 inches, and between about 0.003 inches and about 0.025 inches and be within the spirit and scope of the present invention.

In an embodiment of the present invention, the diameter of the proximal end 31 of the elongated probe 15 is about 0.018 inches. In another embodiment of the present invention, the diameter of the proximal end 31 of the probe 15 is about 0.025 inches. In other embodiments of the present invention, the diameter of the proximal end 31 of the probe 15 varies between about 0.003 inches and about 0.025 inches. Those skilled in the art will recognize the elongated probe 15 can have a diameter at the proximal end 31 smaller than about 0.003 inches, larger than about 0.025 inches, and between about 0.003 inches and about 0.025 inches and be within the spirit and scope of the present invention.

In an embodiment of the present invention, the diameter of the elongated ultrasonic probe 15 is approximately uniform from the proximal end 31 to the distal end 24 of the probe 15. In another embodiment of the present invention, the diameter of the elongated ultrasonic probe 15 gradually decreases from the proximal end 31 to the distal end 24. In an embodiment of the present invention, the probe may resemble a wire. In an embodiment of the present invention, the gradual change of the diameter from the proximal end 31 to the distal end 24 occurs over a plurality of transitions 82 with each transition 82 having an approximately equal length. In another embodiment of the present invention, the gradual change of the diameter from the proximal end 31 to the distal end 24 occurs over a plurality of transitions 82 with each transition 82 having a varying length. The transition 82 refers to a section where the diameter varies from a first diameter to a second diameter. In one embodiment of the present invention, the transition 82 has a length of about 1.125 inches. In another embodiment of the present invention, the transition 82 has a length of about 5.20 inches. In other embodiments of the present invention, the transition 82 has a length between about 1.125 inches and about 5.20 inches. Those skilled in the art will recognize the diameter of the elongated probe 15 can gradually change from the proximal end 31 to the distal end 24 over an at least one transition 82 having a length smaller than about 1.125 inches, greater than about 5.20 inches, and a length between about 1.125 inches and about 5.20 inches and be within the spirit and scope of the present invention.

As shown in FIG. 2B, the diameter of the probe 15 decreases from the proximal end 31 to the distal end 24 over a plurality of intervals 26, 28, 30 and 32 through the plurality of transitions 82. In a preferred embodiment of the present invention, the transitions 82 are gradual. In another embodiment of the present invention, the diameter of the probe 15 slowly tapers from a first larger diameter at the proximal end 31 to a second smaller diameter at the distal end 24 over a length of the probe 15. In another embodiment of the present invention, the diameter of the probe 15 decreases from the proximal end 31 to the distal end 24 through the plurality of transitions 82 that are abrupt and stepwise. Those skilled in the art will recognize that the probe 15 can have the plurality of transitions 82 with different configurations and lengths and be within the spirit and scope of the present invention.

In a preferred embodiment of the present invention, the elongated probe 15 comprises a material of high radiopacity and a material of low radiopacity. In another embodiment of the present invention, the elongated probe 15 comprises a material of high radiopacity. The material of high radiopacity allows the elongated probe to be detected during a medical procedure which includes an imaging procedure. Those skilled in the art will recognize a probe can be composed of many combinations of a material of high radiopacity and a material of low radiopacity and those combinations are within the spirit and scope of the present invention.

Materials of high radiopacity do not allow the passage of a substantial amount of x-rays or other radiation. A material of high radiopacity allows a higher degree of visibility in an imaging procedure than a material of low radiopacity. The radiopacity of various materials results in radiographs showing different radiopacities so the materials can be differentiated. Radiographic interpretation is based on the visualization and analysis of opacities on a radiograph. As x-ray photons move through the body, the x-ray photons will be attenuated by the tissue and some x-ray photons will pass through the tissue to interact with and expose the radiographic film. The greater the amount of tissue absorption, the fewer the number of x-ray photons reaching the film and the higher the degree of visibility of the material on the radiograph.

The absorption of x-rays is a function of the atomic number and thickness of the material. Materials with a higher atomic number will absorb more radiation than materials with a lower atomic number. The atomic number indicates the internal structure for the atom of each element and the atomic number corresponds to the number of protons in the nucleus of an atom of that element. The atomic number also corresponds to the number of electrons in the neutral atom. The larger the number of electrons floating around the nucleus of a material, the higher the radiopacity is of that material. The mean excitation energy is used in comparing the relative radiopacity of elements. Elements with low radiopacity include hydrogen, helium and titanium. Hydrogen (atomic number of 1), has a mean excitation energy of 19.2 electron-volts and helium (atomic number of 2), has a mean excitation energy of 41.8 electron-volts. Titanium (atomic number of 22) has a mean excitation energy of 233 electron-volts. Materials with high radiopacity include, uranium, lead, gold, tantalum and tungsten. Uranium (atomic number of 92), has a mean excitation energy of 890 electron-volts, lead (atomic number of 82) has a mean excitation energy of 823 electron-volts and gold (atomic number of 79) has a mean excitation energy of 790 electron-volts. Tantalum (atomic number of 73) has a mean excitation energy of 718 electron-volts and tungsten (atomic number of 74) has a mean excitation energy of 727 electron-volts. Other materials of high radiopacity that could be used within the spirit and scope of the present invention include molybdenum and alloys thereof. Those skilled in the art will recognize that other materials of high radiopacity known in the art would be within the spirit and scope of the present invention.

The thickness of a material also affects the radiopacity of the materials. Thicker materials will absorb more x-rays than thinner materials of similar composition. Larger diameter materials will have higher radiopacity than smaller diameter materials of similar composition. In a preferred embodiment, the elongated ultrasonic probe of the present invention has a small diameter.

An apparatus and method for radiopaque coatings for an ultrasonic medical device are described in Assignee's co-pending patent application U.S. Ser. No. 10/207,468 which is hereby incorporated herein by reference. U.S. Ser. No. 10/207,468 provides an apparatus and method for using an elongated probe in conjunction with a radiopaque ink to improve the visibility of the probe when used in a medical procedure.

The elongated ultrasonic probe 15 of the present invention is either a single diameter wire with a substantially uniform cross section offering flexural stiffness along its entire length, or transitions along the length of the probe 15 to control the amplitude of the transverse wave along the longitudinal axis of the probe 15. In a preferred embodiment of the present invention, the elongated probe is flexible. In one embodiment, the elongated probe 15 can be cross sectionally non-cylindrical and capable of providing both flexural stiffness and support a transverse wave along its length. The length of the elongated probe 15 of the present invention is chosen so as to be resonant in a transverse mode. In an embodiment of the present invention, the elongated probe 15 is between about 30 centimeters and about 300 centimeters in length. In an embodiment of the present invention, the probe may take the form of a wire. Those skilled in the art will recognize a probe can have a length shorter than about 30 centimeters and a length longer than about 300 centimeters and be within the spirit and scope of the present invention.

The elongated, ultrasonic probe 15 is inserted into a vasculature of the body and may be disposed of after use. In a preferred embodiment of the present invention, the elongated, ultrasonic probe 15 is for a single use and on a single patient. In a preferred embodiment of the present invention, the elongated, ultrasonic probe is disposable. In another embodiment of the present invention, the elongated, ultrasonic probe can be used multiple times.

Figure 3:
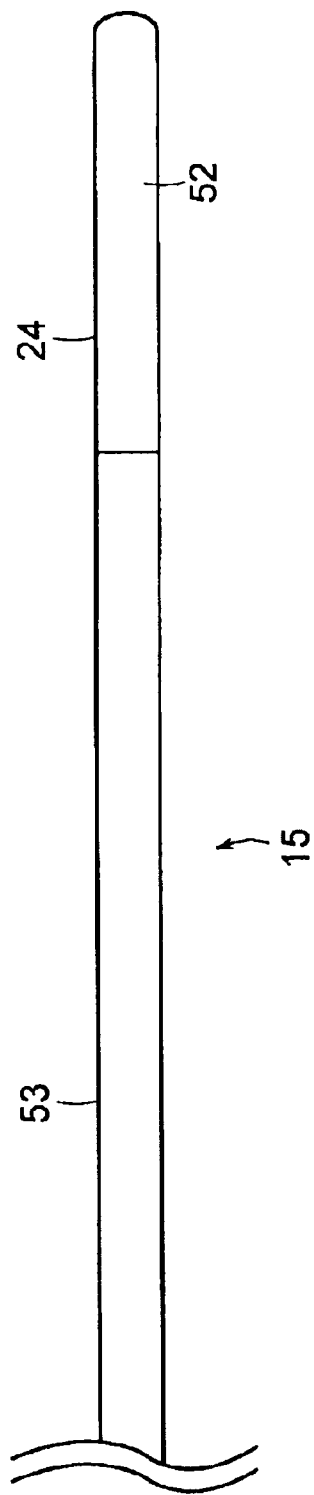
FIG. 3 shows a fragmentary view of a distal end of an elongated, ultrasonic probe of the present invention having a material of high radiopacity at the distal end.

FIG. 3 shows a fragmentary view of a preferred embodiment of the present invention wherein the elongated probe 15 has a material with high radiopacity 52 at a distal end 24 of the probe 15 and a material with low radiopacity 53 engaging the material with high radiopacity 52. The material of high radiopacity 52 is at a predetermined location of the probe 15. The material of high radiopacity 52 is capable of withstanding a series of vibrations of the probe 15 and allows the elongated probe 15 to be visualized in imaging procedures. In a preferred embodiment of the present invention shown in FIG. 3, the probe 15 comprises a material of high radiopacity 52 and a material of low radiopacity 53. In another embodiment of the present invention, the entire length of the probe 15 is comprised of a material of high radiopacity 52. Those skilled in the art will recognize a probe can be composed of many combinations of a material of high radiopacity and a material of low radiopacity that are within the spirit and scope of the present invention.

The material of high radiopacity 52 is biocompatible, non-toxic and easily manufacturable. The material of high radiopacity 52 does not allow the passage of a substantial amount of x-rays or other radiation and allows for the probe 15 to be detected, visualized and image enhanced when inserted into a body during a medical procedure including an imaging procedure. The material of high radiopacity 52 allows for the probe 15 to be visualized and facilitates diagnostic and therapeutic treatments. The use of a material of low radiopacity 53 and a material of high radiopacity 52 in comprising the probe 15 allows the ultrasonic medical device 11 to benefit from the high capacitance properties of the material of low radiopacity 53 and the ability of the material of high radiopacity 52 to absorb radiation to allow for the probe 15 to be visualized during an imaging procedure. In a preferred embodiment of the present invention, the material of high radiopacity 52 is tantalum. In another embodiment of the present invention, the material of high radiopacity 52 is a tantalum alloy. Other materials of high radiopacity 52 that could be used within the spirit and scope of the present invention include, but are not limited to, tungsten, gold, molybdenum and alloys thereof. Those skilled in the art will recognize that other materials of high radiopacity 52 known in the art would be within the spirit and scope of the present invention.

In a preferred embodiment of the present invention shown in FIG. 3, the material with high radiopacity 52 comprises tantalum. Tantalum is a greyish silver, heavy metal that has a history of uses in prosthetic devices including, but not limited to, hips and plates in skulls. The biocompatability of tantalum is known in the art. Tantalum has superior corrosion resistance and is immune to attack by body fluids. Tantalum has a high melting point (3017° C.) and dissolves into materials of lower melting point including, but not limited to, titanium.

In another embodiment of the present invention, the material of high radiopacity 52 is tungsten. Tungsten is a steel-gray to tin-white metal that has excellent corrosion resistance and is attacked only slightly by most mineral acids. Tungsten is known in the art to be used in x-ray targets.

In a preferred embodiment of the present invention shown in FIG. 3, the material of low radiopacity 53 is titanium or a titanium alloy. Titanium is a low density metal that is known in the art to be used as a structural material. Titanium has good strength and is easily fabricated. Titanium and its alloys have excellent corrosion resistance in many environments and have good elevated temperature properties. Titanium has a lower melting point (1688° C.) than tantalum (3017° C.). In another embodiment of the present invention, the material of low radiopacity 53 is stainless steel. In another embodiment of the present invention, the material of low radiopacity 53 is a combination of titanium and stainless steel. Those skilled in the art will recognize that other materials of low radiopacity 53, or combinations of materials having low radiopacity 53, known in the art would be within the spirit and scope of the present invention.

The material of high radiopacity 52 is easily manufacturable and allows for engagement to the elongated probe 15 at predetermined locations. In a preferred embodiment of the present invention shown in FIG. 3, the elongated probe 15 is comprised such that a material with high radiopacity 52 is engaged to a material with low radiopacity 53 at the distal end 24 of the probe 15. In the preferred embodiment shown in FIG. 3, the elongated probe 15 comprises a material with high radiopacity 52 and a material with low radiopacity 53. The material with high radiopacity 52 is engaged to the material with low radiopacity 53 of the probe 15 through processes including, but not limited to, mechanically engaging and metallurgically engaging. The more specific processes of engaging two materials include, but are not limited to, butt-welding, brazing, shrink fitting, lap welding, threaded fitting, twisting the materials and other mechanical or metallurgical connections. Those skilled in the art will recognize that other processes known in the art of engaging a material of high radiopacity and a material of low radiopacity would be within the spirit and scope of the present invention.

In a preferred embodiment of the present invention shown in FIG. 3, a material with high radiopacity 52 is engaged to a material with low radiopacity 53 of the elongated probe 15 by a process of butt-welding. Butt-welding is welding together two parts placed end to end. It can be accomplished by electrical resistance, electron beam, electric arc, induction, flame or any other means to generate heat at the junction. Those skilled in the art will recognize that additional steps may be added to the butt-welding process and still be within the spirit and scope of the present invention.

In another embodiment of the present invention, a material with high radiopacity 52 is engaged to a material with low radiopacity 53 of the elongated probe 15 by a process of brazing. Brazing is a process whereby two metals are joined through the use of heat and a brazing material. In an embodiment of the present invention, the brazing material is, but is not limited to, nickel, molybdenum or a nickel stainless steel. Those skilled in the art will recognize that other brazing materials could be used that would still be within the spirit and scope of the present invention. Those skilled in the art will recognize that additional steps may be added to the brazing process and still be within the spirit and scope of the present invention.

In another embodiment of the present invention shown in FIG. 3, a material with high radiopacity 52 is engaged to a material with low radiopacity 53 of the elongated probe 15 by a process of shrink fitting. Shrink fitting is a procedure in which one metal is inserted into the other through the use of heat to produce a strong joint between the metals. In the process, heating one metal causes the metal to expand or contract on to the other, thereby mechanically holding the pieces together through interference and pressure. Those skilled in the art will recognize that additional steps may be added to the shrink fitting process and still be within the spirit and scope of the present invention.

In another embodiment of the present invention, the material with high radiopacity 52 is engaged to the material with low radiopacity 53 of the elongated probe 15 by a process of lap welding. Lap welding consists of continuous welding on the outside surfaces only, leaving the plates lapped on the inside. Those skilled in the art will recognize that additional steps may be added to the lap welding process and still be within the spirit and scope of the present invention.

In an embodiment of the present invention, the material with high radiopacity 52 is engaged to the material with low radiopacity 53 of the elongated probe 15 by a process of twisting the materials together. In this process, the material of high radiopacity 52 and material of low radiopacity 53 are mechanically placed in close proximity to one another. In one embodiment of the present invention, the twisting process results in the material of high radiopacity 52 and the material of low radiopacity 53 not touching one another. In an embodiment of the present invention, the material with high radiopacity 52 or the material with low radiopacity 53 can be coated with a coating. In another embodiment of the present invention, the material with high radiopacity 52 and the material with low radiopacity 53 can be coated with a coating. Those skilled in the art will recognize that other processes for engaging two materials with the materials not touching one another are within the spirit and scope of the present invention. In another embodiment of the present invention, the twisting process results in the material of high radiopacity and the material of low radiopacity touching one another. Those skilled in the art will recognize that other twisting processes may be used within the spirit and scope of the present invention.

In a preferred embodiment of the present invention, the small diameter of the elongated probe 15 is not equal as the probe 15 extends from a proximal end to a distal end 24. In another embodiment of the present invention, the small diameter of the elongated probe 15 is approximately equal along the length of the probe 15. An elongated probe 15 with a small diameter that is approximately constant or a small diameter that gradually tapers from the proximal end to the distal end 24 enables facile insertion into highly occluded or narrow interstices within a blood vessel and enables transfer and/or coupling of ultrasonic energy. Those skilled in the art will recognize that a probe can be composed of many different combinations of diameters and still be within the spirit and scope of the present invention.

The material with high radiopacity 52 does not allow the passage of a substantial amount of x-rays or other radiation and allows for the elongated probe 15 to be detected, visualized and image enhanced when inserted into a body during a medical procedure which includes an imaging procedure. Imaging procedures include, but are not limited to, fluoroscopy, conventional radiography, tomography, digital x-ray imaging, ultrasound, magnetic resonance imaging (MRI) and other image modalities. The improved visibility of the probe 15 facilitates diagnostic and therapeutic treatments. Those skilled in the art will recognize that other imaging procedures known in the art would be within the spirit and scope of the present invention.

Fluoroscopy is another method of seeing and imaging the interior of the body similar to x-ray. A continuous x-ray beam is passed through the body part being examined, and is transmitted to a television-like monitor so that the body part and its motion can be seen in detail. Fluoroscopy is used in many types of examinations and procedures, such as barium x-rays, cardiac catheterization, and placement of intravenous (IV) catheters (hollow tubes into veins or arteries). In barium x-rays, fluoroscopy allows the physician to see the movement of the intestines as the barium moves through them. In cardiac catheterization, fluoroscopy enables the physician to see the flow of blood through the coronary arteries in order to evaluate the presence of arterial blockages. For intravenous catheter insertion, fluoroscopy assists the physician in guiding the catheter into a specific location inside the body. Fluoroscopy helps diagnose problems with the digestive tract, the bowel, kidneys, gallbladder, stomach, upper gastrointestinal tract and joints. Fluoroscopy is used during many diagnostic and therapeutic radiologic procedures to observe the action of instruments being used either to diagnose or to treat a patient.

Fluoroscopic imaging is useful when it is necessary to radiograph a dynamic situation. Fluoroscopy is most commonly used to evaluate the gastrointestinal tract but can also be used to record the motion of any other body part in which the component in motion might be helpful in arriving at a diagnostic decision. A fluoroscope is a radiographic machine which has an x-ray tube mounted in a way that the beam can pass through the patient and be recorded on a fluorescent screen. In fluoroscopes, the observer does not look directly at the fluoroscope screen but looks at a video image produced from a video camera which is focused on the screen. Fluoroscopes also incorporate a spot film device which allows the operator to move a film into the beam and take "snap shot" pictures of any abnormality which is observed. Fluoroscopes usually attach to an x-ray table which allows the operator to tilt the patient or camera in various directions and the x-ray tube is most commonly positioned under the table top with the spot film device and the fluorescent screen including an image intensifier being above the patient if the patient is lying supine on the table.

Conventional radiography is a procedure that uses standard x-rays to analyze the bony and soft tissue anatomy for diagnosis. Tomography is a series of x-rays that focus on a specific level within the body and give precise and detailed images of selected organs, bony structures and tissues. Digital x-ray imaging is a technique in which an x-ray is passed through a body to a photoconductor where it is instantly converted to an electronic signal that produces a digital image on a computer screen. Ultrasound is a medical imaging technique that uses high frequency sound waves and echoes to look at the organ being examined. Magnetic resonance imaging (MRI) is an imaging technique used primarily in medical settings to produce high quality images of the inside of the human body.

Figure 4:
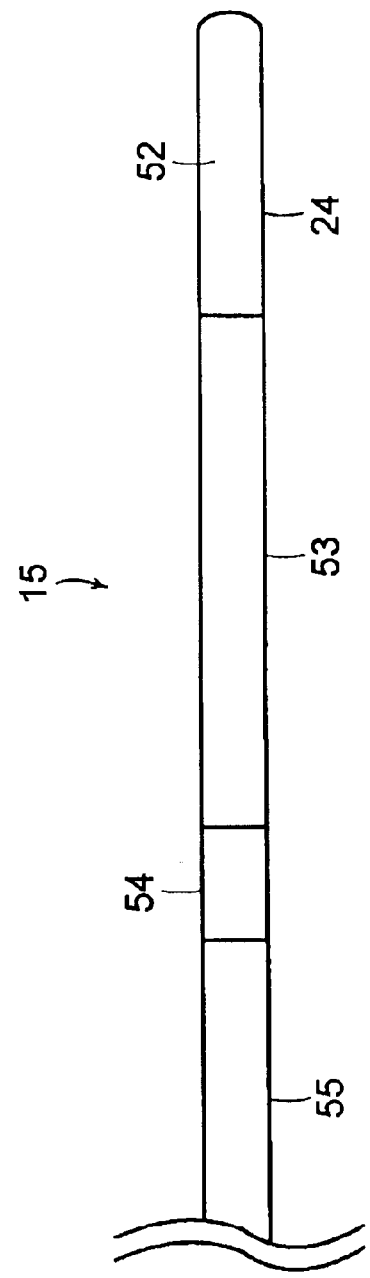
FIG. 4 shows a fragmentary view of an alternative embodiment of the present invention having a material of high radiopacity at a plurality of predetermined locations of the elongated, ultrasonic probe.

FIG. 4 shows a probe 15 of the present invention with a plurality of predetermined locations having a material with high radiopacity 52,54. The probe 15 comprises a plurality of lengths having a material with low radiopacity 53,55. In an embodiment of the present invention, the lengths of the predetermined locations having a material with high radiopacity 52,54 are approximately equal. In another embodiment of the present invention, the lengths of the predetermined locations having a material with high radiopacity 52,54 are not equal. In an embodiment of the present invention, the lengths having a material with low radiopacity 53,55 are approximately equal. In another embodiment of the present invention, the lengths having a material with low radiopacity 53,55 are not equal. In an embodiment of the present invention, the distances between the material with high radiopacity 52,54 and the material with low radiopacity 53,55 are approximately equal. In another embodiment of the present invention, the distances between the material with high radiopacity 52,54 and the material with low radiopacity 53,55 are not equal. In an embodiment of the present invention, the length of the material with low radiopacity 53 is about one inch. Those skilled in the art will recognize a probe can be composed of many different lengths of a material with high radiopacity and many different lengths of a material with low radiopacity and still be within the spirit and scope of the present invention.

In the embodiment of the present invention shown in FIG. 4, the elongated probe 15 is comprised of a material with high radiopacity 52,54 and a material with low radiopacity 53,55. The use of a material of low radiopacity and a material of high radiopacity in comprising the probe 15 allows the ultrasonic medical device 11 to benefit from the high capacitance properties of the material of low radiopacity and the ability of the material of high radiopacity to absorb radiation to allow for the probe 15 to be better visualized during a medical procedure which includes an imaging procedure.

In an embodiment of the present invention, the small diameter of the elongated probe 15 gradually tapers from a proximal end to a distal end of the probe 15. The gradual taper of the small diameter, elongated probe 15 enables facile insertion into highly occluded or extremely narrow interstices in the body (i.e., within a blood vessel). In a preferred embodiment of the present invention, the small diameter of the elongated probe 15 is not equal along the length of the probe 15. In an embodiment of the present invention, the small diameter of the elongated probe 15 is approximately equal along the length of the probe 15. A small and approximately uniform diameter of an elongated probe 15 enables facile insertion into highly occluded or extremely narrow interstices in the body (i.e., within a blood vessel). In an embodiment of the present invention, the small diameter of the material with high radiopacity 52,54 is approximately equal to the small diameter of the material with low radiopacity 53,55 along the length of the probe 15. In an embodiment of the present invention, the small diameter of the material with high radiopacity 52,54 is not equal to the small diameter of the material with low radiopacity 53,55 along the length of the probe 15. In an embodiment of the present invention, the small diameter of a material with high radiopacity 52,54 is not equal along the length of the probe 15. In an embodiment of the present invention, the small diameter of a material with high radiopacity 52,54 is approximately equal along the length of the probe 15. In an embodiment of the present invention, the small diameter of a material with low radiopacity 53,55 is not equal along the length of the probe 15. In an embodiment of the present invention, the small diameter of a material with low radiopacity 53,55 is approximately equal along the length of the probe 15. Those skilled in the art will recognize that a probe can be composed of many different combinations (varying and approximately uniform) of diameters and still be within the spirit and scope of the present invention.

The material of high radiopacity 52,54 of the present invention shown in FIG. 4, is capable of withstanding a series of vibrations of the probe 15 and does not allow the passage of a substantial amount of x-rays or other radiation. The material of high radiopacity 52,54 is biocompatible, non-toxic and easily manufacturable.

The material with high radiopacity 52,54 is engaged to the material with low radiopacity 53,55 through a series of processes including, but not limited to, butt-welding, brazing, shrink fitting, lap welding, threaded fitting and twisting the materials. In an embodiment of the present invention, the processes of engaging the material with high radiopacity 52,54 and the material with low radiopacity 53,55 is the same. In another embodiment of the present invention, the processes of engaging the material with high radiopacity 52,54 and the material with low radiopacity 53,55 is not the same. Those skilled in the art will recognize that other processes of engaging a material of high radiopacity and a material of low radiopacity known in the art would be within the spirit and scope of the present invention.

FIG. 5 shows a fragmentary view of the probe 15 of the present invention with a length of a composite section 62 of both a material of high radiopacity and a material of low radiopacity at the distal end 24 of the probe 15. In an embodiment of the present invention shown in FIG. 5, the composite section is engaged to the probe 15 at a material with low radiopacity 53. In another embodiment of the present invention, the entire length of the probe 15 is comprised of a composite section 62 including both a material of high radiopacity and a material of low radiopacity. Those skilled in the art will recognize a probe can be comprised of many combinations of a material of high radiopacity and a material of low radiopacity and are within the spirit and scope of the present invention.

Figure 6:
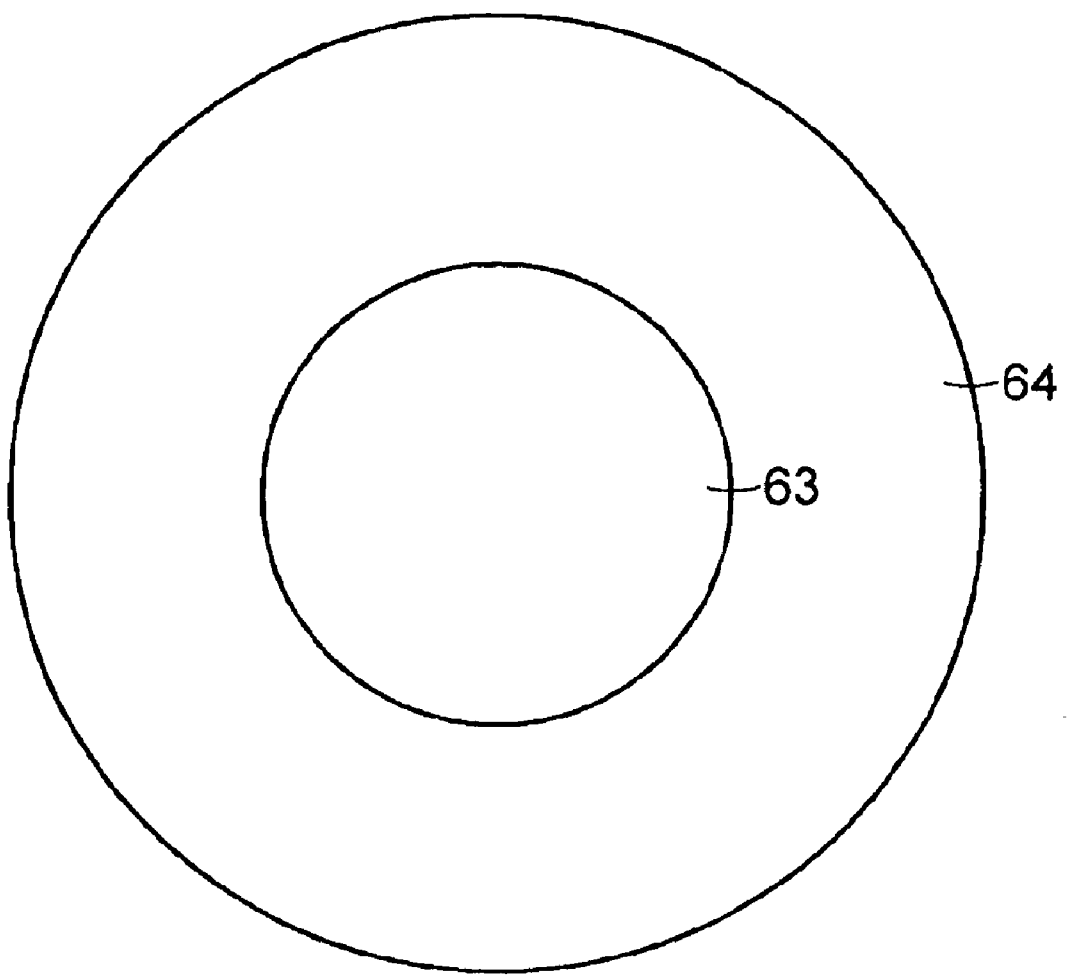
FIG. 6 shows a sectional view of a distal end of an elongated, ultrasonic probe of the present invention as seen from a line A—A of FIG. 5.

FIG. 6 shows a sectional view of a distal end 24 of the elongated probe 15 of the present invention as seen from line A—A of FIG. 5. In an embodiment of the present invention shown in FIG. 6, the cross section is approximately circular with an outside area of a material of high radiopacity 64 and an inner member of a material of low radiopacity 63. In another embodiment of the present invention, the cross section is approximately circular with an outside area of a material of low radiopacity 63 and an inner member of a material of high radiopacity 64. In other embodiments of the present invention, the shape of the cross section of the probe 15 includes, but is not limited to, square, trapezoidal, oval, triangular, circular with a flat portion and similar cross sections. The material of high radiopacity 64 allows for detection of the elongated probe 15 when the elongated probe 15 is inserted into a vasculature of the body during a medical procedure including an imaging procedure. Those skilled in the art will recognize that other cross sectional geometric configurations known in the art would be within the spirit and scope of the present invention.

FIG. 7 shows an elongated probe 15 of the present invention with a plurality of predetermined locations of composite sections 62, 66 having a material of high radiopacity and a material of low radiopacity of the elongated probe 15. The elongated probe 15 comprises a material with low radiopacity 53,55. In an embodiment of the present invention, the lengths of composite sections 62,66 are approximately equal. In another embodiment of the present invention, the lengths of composite sections 62, 66 are not equal. In an embodiment of the present invention, the lengths of the material with low radiopacity 53,55 are approximately equal. In another embodiment of the present invention, the lengths of the material with low radiopacity 53,55 are not equal. In an embodiment of the present invention, the distances between the composite sections 62,66 and the material with low radiopacity 53,55 are approximately equal. In another embodiment of the present invention, the distances between the composite sections 62,66 and the material with low radiopacity 53,55 are not equal. Those skilled in the art will recognize a probe can be composed of many different lengths of composite sections and materials with low radiopacity and still be within the spirit and scope of the present invention.

In an embodiment of the present invention, it is desirable that the small diameter of the probe 15 be approximately constant or gradually taper from a proximal end to a distal end of the probe 15. The constant or gradual taper of the small diameter, elongated probe 15 enables facile insertion into highly occluded or extremely narrow interstices in the body (i.e. within a blood vessel). The embodiment shown in FIG. 7 includes an elongated probe 15 with composite sections 62,66 and a material with low radiopacity 53,55. In an embodiment of the present invention, the small diameters of composite sections 62,66 and the material with low radiopacity 53,55 are approximately equal along the length of the probe 15. In another embodiment of the present invention, the small diameters of the composite sections 62,66 and the material with low radiopacity 53,55 are not equal along the length of the probe 15. In an embodiment of the present invention, the small diameters of the material with low radiopacity 53,55 are approximately equal. In an embodiment of the present invention, the small diameter of the material with low radiopacity 53, 55 are not equal. In an embodiment of the present invention, the small diameters of composite sections 62,66 are approximately equal. In an embodiment of the present invention, the small diameters of composite sections 62, 66 are not equal. Those skilled in the art will recognize that a probe can be composed of many different combinations of diameters (i.e., varying and approximately uniform along the length of the probe) and still be within the spirit and scope of the present invention.

The materials of high radiopacity comprising composite sections 62,66 of the present invention shown in FIG. 7, are capable of withstanding a series of vibrations of the probe 15 and do not allow the passage of a substantial amount of x-rays or other radiation. The materials of high radiopacity are biocompatible, non-toxic and easily manufacturable.

Figure 8:
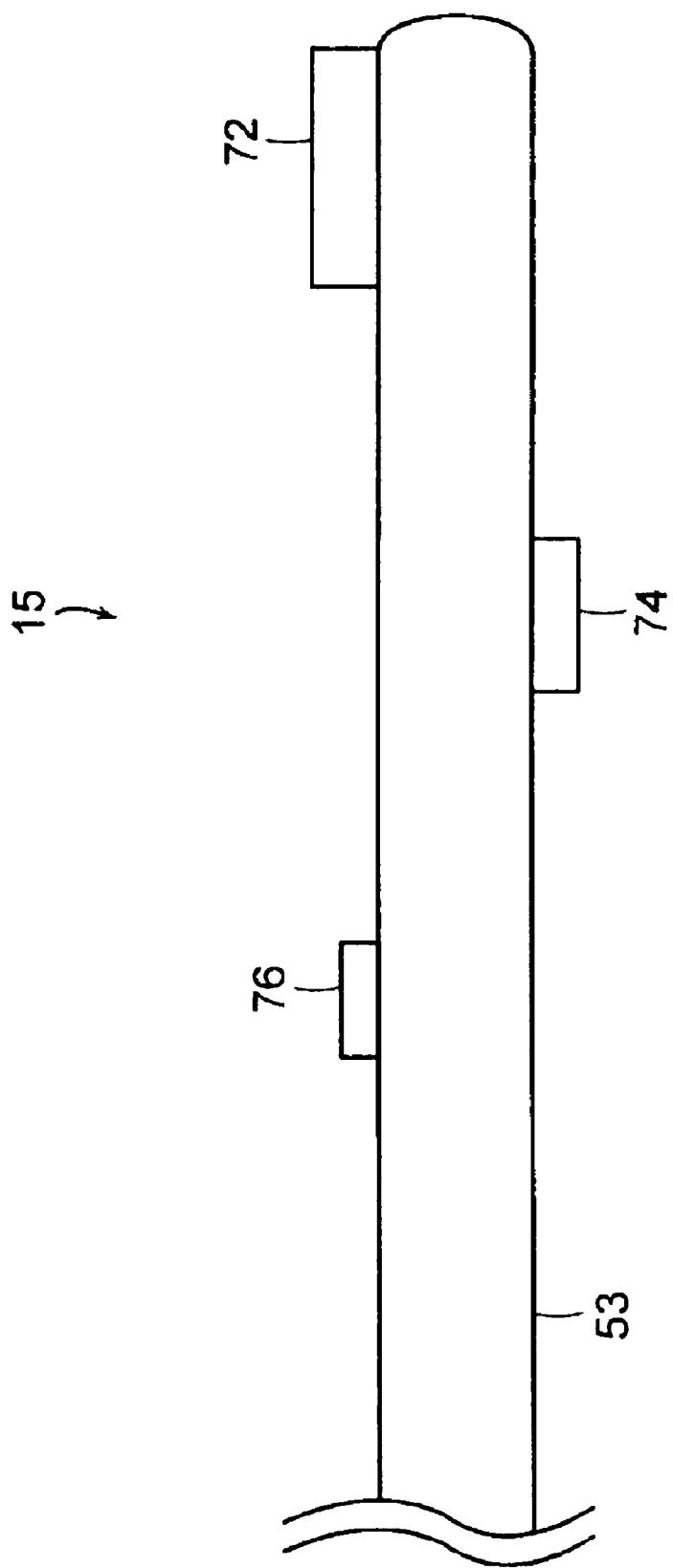
FIG. 8 shows a fragmentary view of an alternative embodiment of the present invention wherein an elongated, ultrasonic probe has a material of high radiopacity at a plurality of predetermined locations of the elongated, ultrasonic probe.

FIG. 8 shows an alternative embodiment of the present invention wherein the elongated probe 15 comprises a material with high radiopacity 72, 74, 76 at a plurality of predetermined locations of the probe 15. The elongated probe 15 comprises a material with low radiopacity 53. Geometric configurations of the material with high radiopacity 72, 74, 76 include, but are not limited to circular, square, trapezoidal, triangular, circular with a flat portion or similar cross sections. In an embodiment of the present invention, the small diameter of the elongated probe gradually tapers from a proximal end to a distal end. In an embodiment of the present invention, the small diameter of the elongated probe 15 is approximately the same along the length of the probe 15. The small diameter at the predetermined locations of the material with high radiopacity 72, 74, 76 is approximately equal to the small diameter of the material with low radiopacity 53 along the length of the probe 15. In another embodiment of the present invention shown in FIG. 8, the small diameters of a material with high radiopacity 72, 74, 76 and the small diameter of a material with low radiopacity 53 are not equal along the length of the probe 15.

FIG. 8 shows a probe 15 of the present invention with a plurality of predetermined locations of a material with high radiopacity 72, 74, 76. The probe 15 comprises a material with low radiopacity 53. In an embodiment of the present invention, the lengths of the predetermined locations of the material with high radiopacity 72, 74, 76 are approximately equal. In another embodiment of the present invention, the lengths of the predetermined locations of the material with high radiopacity 72, 74, 76 are not equal. In an embodiment of the present invention, the distance between the material with high radiopacity 72, 74, 76 is approximately equal. In another embodiment of the present invention, the distance between the material with high radiopacity 72, 74, 76 is not equal. Those skilled in the art will recognize a probe can be composed of many different lengths of a material with high radiopacity and many different lengths of a material with low radiopacity and still be within the spirit and scope of the present invention.

The present invention also provides a method of improving the visibility of an ultrasonic device during a medical procedure including an imaging procedure by engaging a material of high radiopacity to an elongated probe wherein the material of high radiopacity engages the elongated probe at an at least one predetermined location. The material of high radiopacity engages the elongated probe by processes including, but not limited to, butt-welding, brazing, shrink fitting, lap welding, threaded fitting, twisting the materials or other mechanical or metallurgical connections. Those skilled in the art will recognize that other processes of engaging a material of high radiopacity and a material of low radiopacity known in the art would be within the spirit and scope of the present invention.

The material of high radiopacity allows the detection of the elongated probe 15 during a medical procedure which includes an imaging procedure. Imaging procedures include, but are not limited to, fluoroscopy, conventional radiography, tomography, digital x-ray imaging, ultrasound, magnetic resonance imaging (MRI) and other image modalities. Those skilled in the art will recognize that other imaging procedures known in the art would be within the spirit and scope of the present invention.

The present invention provides a method of improving the visibility of an elongated probe having a small diameter comprising engaging a material of high radiopacity at a plurality of predetermined locations of the elongated probe. The material of high radiopacity allows for the detection of the elongated probe in medical procedures which include an imaging procedure.

The apparatus and the method of the present invention are useful in procedures including, but not limited to, barium x-rays, cardiac catheterization, and placement of intravenous (IV) catheters (hollow tubes into veins or arteries). In barium x-rays, fluoroscopy allows the physician to see the movement of the intestines as the barium moves through them. In cardiac catheterization, fluoroscopy enables the physician to see the flow of blood through the coronary arteries in order to evaluate the presence of arterial blockages. For intravenous catheter insertion, fluoroscopy assists the physician in guiding the catheter into a specific location inside a body. The present invention may also diagnose problems with the digestive tract, the bowel, kidneys, gallbladder, stomach, upper gastrointestinal tract and joints. The apparatus and method of the present invention will facilitate a physician's ability to observe the action of an instrument being used either to diagnose or to treat a patient.

The present invention provides an apparatus and method for a medical device having an elongated probe comprised of a material of low radiopacity with a material of high radiopacity engaged at an at least one predetermined location of the elongated probe in order to improve the visibility of the probe when used in a medical procedure including an imaging procedure. The material of high radiopacity allows for the elongated probe to be detected when inserted into a vasculature of a body when using imaging procedures including, but not limited to, fluoroscopy, conventional radiography, tomography, digital x-ray imaging, ultrasound, magnetic resonance imaging (MRI) and other image modalities. The material of high radiopacity is capable of withstanding a series of vibrations of the elongated probe. The present invention provides an apparatus and method for an ultrasonic medical device with improved visibility in imaging procedures that is simple, user-friendly, reliable and cost-effective.

All references, patents, patent applications and patent publications cited herein are hereby incorporated herein by reference in their entireties. Variations, modifications, and other implementations of what is described herein will occur to those of ordinary skill in the art without departing from the spirit and scope of the present invention as claimed. Accordingly, the present invention is to be defined not by the preceding illustrative description but instead by the spirit and scope of the following claims.

What is claimed is:

1. An ultrasonic medical device for destroying a biological material comprising:
    an elongated, ultrasonic flexible probe having a proximal end, a distal end and a longitudinal length therebetween; and
    a material of high radiopacity at an at least one predetermined location on an outside surface of the longitudinal length of the elongated, ultrasonic flexible probe, said probe adapted such that a transverse ultrasonic vibration along the longitudinal length of the elongated ultrasonic probe produces a plurality of nodes and a plurality of anti-nodes causing a biological material destroying effect along at least a portion of the longitudinal length including the material of high radiopacity.

2. The device of claim 1 wherein the material of high radiopacity comprises tantalum.

3. The device of claim 1 wherein the material of high radiopacity comprises a tantalum alloy.

4. The device of claim 1 wherein the material of high radiopacity is selected from the group consisting of tantalum, tungsten, gold, molybdenum and alloys thereof.

5. The device of claim 1 wherein the material of high radiopacity is biocompatible.

6. The device of claim 1 wherein the elongated, ultrasonic flexible probe comprises titanium.

7. The device of claim 1 wherein the elongated, ultrasonic flexible probe comprises a material of low radiopacity.

8. The device of claim 1 wherein the elongated, ultrasonic flexible probe comprises a material of high radiopacity.

9. The device of claim 1 wherein the elongated, ultrasonic flexible probe is comprised substantially of the material of high radiopacity.

10. The device of claim 1 wherein the elongated, ultrasonic flexible probe comprises the material of high radiopacity and a material of low radiopacity.

11. The device of claim 1 wherein the material of high radiopacity engages the elongated, ultrasonic flexible probe at a plurality of predetermined locations.

12. The device of claim 11 wherein a length of the plurality of predetermined locations of the material of high radiopacity is approximately equal.

13. The device of claim 11 wherein a length of the plurality of predetermined locations of the material of high radiopacity is unequal.

14. The device of claim 11 wherein a distance between the plurality of predetermined locations of the material of high radiopacity is approximately equal.

15. The device of claim 11 wherein a distance between the plurality of predetermined locations of the material of high radiopacity is unequal.

16. The device of claim 1 wherein the material of high radiopacity is located at the distal end of the elongated, ultrasonic flexible probe.

17. The device of claim 1 wherein the elongated, ultrasonic flexible probe has a diameter that enables insertion of the elongated, ultrasonic flexible probe into a vasculature of a body.

18. The device of claim 1 wherein the elongated, ultrasonic flexible probe comprises a substantially uniform diameter from the proximal end of the elongated, ultrasonic flexible probe to the distal end of the elongated, ultrasonic flexible probe.

19. The device of claim 1 wherein the elongated, ultrasonic flexible probe comprises a varying diameter from the proximal end of the elongated, ultrasonic flexible probe to the distal end of the elongated, ultrasonic flexible probe.

20. The device of claim 1 further comprising a plurality of transitions along the longitudinal length of the elongated, ultrasonic flexible probe to change a diameter from the proximal end to the distal end.

21. The device of claim 20 wherein the plurality of transitions gradually change the diameter from the proximal end to the distal end along the longitudinal length of the elongated, ultrasonic flexible probe.

22. The device of claim 20 wherein the plurality of transitions are stepwise to change the diameter from the proximal end to the distal end along the longitudinal length of the elongated, ultrasonic flexible probe.

23. The device of claim 1 wherein a diameter of the elongated, ultrasonic flexible probe slowly tapers from the proximal end to the distal end along the longitudinal length of the elongated, ultrasonic flexible probe.

24. The device of claim 1 wherein the elongated, ultrasonic flexible probe has a small cross sectional profile.

25. The device of claim 1 wherein the elongated, ultrasonic flexible probe vibrates in a direction transverse to at least a portion of the longitudinal length of the elongated, ultrasonic flexible probe.

26. The device of claim 1 wherein the elongated, ultrasonic flexible probe is for a single use on a single patient.

27. The device of claim 1 wherein the elongated, ultrasonic flexible probe is disposable.

28. An ultrasonic device for destroying a biological material comprising:
    an elongated ultrasonic probe having a small diameter and a longitudinal length; and
    a material having a high radiopacity at a plurality of predetermined locations on an outside surface of the longitudinal length of the elongated ultrasonic probe, said probe adapted such that a transverse ultrasonic vibration along the longitudinal length of the elongated ultrasonic probe produces a plurality of nodes and a plurality of anti-nodes causing a biological material destroying effect along at least a portion of the longitudinal length including the material of high radiopacity.

29. The device of claim 28 wherein the material having a high radiopacity is located at a distal end of the elongated probe.

30. The device of claim 28 wherein the elongated probe has a diameter that enables insertion of the elongated probe into a vasculature of a body.

31. The device of claim 28 wherein the elongated probe comprises a substantially uniform diameter from a proximal end of the elongated probe to a distal end of the elongated probe.

32. The device of claim 28 wherein the elongated probe comprises a varying diameter from a proximal end of the elongated probe to a distal end of the elongated probe.

33. The device of claim 28 wherein the material having a high radiopacity comprises tantalum.

34. The device of claim 28 wherein the material having a high radiopacity comprises a tantalum alloy.

35. The device of claim 28 wherein the material having a high radiopacity is selected from the group consisting of tantalum, tungsten, gold, molybdenum and alloys thereof.

36. The device of claim 28 wherein the material having a high radiopacity is biocompatible.

37. The device of claim 28 wherein a first material having a high radiopacity is located at a first predetermined location and a second material having a high radiopacity is located at a second predetermined location.

38. The device of claim 37 wherein the first material having a high radiopacity and the second material having a high radiopacity are the same.

39. The device of claim 37 wherein the first material having a high radiopacity and the second material having a high radiopacity are different.

40. A method of improving the visibility of an ultrasonic device for destroying a biological material during a medical procedure comprising;
providing a small diameter elongated ultrasonic probe having a longitudinal length;
engaging a material of high radiopacity to the small diameter elongated ultrasonic probe at an at least one predetermined location on an outside surface of the longitudinal length of the small diameter elongated ultrasonic probe; and
adapting the small diameter elongated ultrasonic probe such that a transverse ultrasonic vibration along the longitudinal length of the probe produces a plurality of nodes and a plurality of anti-nodes causing a biological material destroying effect along at least a portion of the longitudinal length including the material of high radiopacity.

41. The method of claim 40 wherein the material of high radiopacity engages the small diameter, elongated probe at a plurality of predetermined locations.

42. The method of claim 41 wherein a distance between the plurality of predetermined locations of the material of high radiopacity is approximately equal.

43. The method of claim 41 wherein a distance between the plurality of predetermined locations of the material of high radiopacity is unequal.

44. The method of claim 41 wherein a length of the plurality of predetermined locations of the material of high radiopacity is approximately equal.

45. The method of claim 41 wherein a length of the plurality of predetermined locations of the material of high radiopacity is unequal.

46. The method of claim 40 wherein the material of high radiopacity is located at a distal end of the small diameter, elongated probe.

47. The method of claim 40 wherein the small diameter, elongated probe has a diameter that enables insertion of the small diameter, elongated probe into a vasculature of a body.

48. The method of claim 40 wherein the small diameter, elongated probe comprises a substantially uniform diameter from a proximal end of the small diameter, elongated probe to a distal end of the small diameter, elongated probe.

49. The method of claim 40 wherein the small diameter, elongated probe comprises a varying diameter from a proximal end of the small diameter, elongated probe to a distal end of the small diameter, elongated probe.

50. The method of claim 40 wherein a first material of high radiopacity is located at a first predetermined location and a second material of high radiopacity is located at a second predetermined location.

51. The method of claim 50 wherein the first material of high radiopacity and the second material of high radiopacity are the same.

52. The method of claim 50 wherein the first material of high radiopacity and the second material of high radiopacity are different.

53. The method of claim 40 wherein the small diameter, elongated probe comprises a plurality of sections of a material with low radiopacity and a plurality of sections of a material with high radiopacity.

54. The method of claim 40 wherein the material of high radiopacity engages the small diameter, elongated probe by a process of butt-welding.

55. The method of claim 40 wherein the material of high radiopacity engages the small diameter, elongated probe by a process of brazing.

56. The method of claim 40 wherein the material of high radiopacity engages the small diameter, elongated probe by a process of shrink fitting.

57. The method of claim 40 wherein the material of high radiopacity engages the small diameter, elongated probe by a process of lap welding.

58. The method of claim 40 wherein the material of high radiopacity engages the small diameter, elongated probe by a process of threaded fitting.

59. The method of claim 40 wherein the material of high radiopacity engages the small diameter, elongated probe by a process of twisting of materials.

60. The method of claim 40 wherein the material of high radiopacity engages the small diameter, elongated probe by a mechanical connection.

61. The method of claim 40 wherein the material of high radiopacity engages the small diameter, elongated probe by a metallurgical connection.

62. The method of claim 40 wherein the material of high radiopacity comprises tantalum.

63. The method of claim 40 wherein the material of high radiopacity comprises a tantalum alloy.

64. The method of claim 40 wherein the material of high radiopacity is selected from the group consisting of tantalum, tungsten, gold, molybdenum and alloys thereof.

65. The method of claim 40 wherein the material of high radiopacity is biocompatible.

66. The method of claim 40 wherein the small diameter, elongated probe comprises titanium.

67. The method of claim 40 wherein the small diameter, elongated probe comprises a material of low radiopacity.

68. The method of claim 40 wherein the small diameter, elongated probe comprises a material of high radiopacity.

69. The method of claim 40 wherein the small diameter, elongated probe is comprised substantially of a material of high radiopacity.

70. The method of claim 40 wherein the small diameter, elongated probe comprises a material of high radiopacity and a material of low radiopacity.

71. The method of claim 40 wherein the small diameter, elongated probe comprises a proximal end, a distal end, a longitudinal length therebetween and a plurality of transitions along the longitudinal length.

72. The method of claim 71 wherein the plurality of transitions along the longitudinal length of the small diameter, elongated probe changes a diameter from the proximal end to the distal end.

73. The method of claim 71 wherein the plurality of transitions gradually change the diameter from a proximal end to a distal end along the longitudinal length of the small diameter, elongated probe.

74. The method of claim 71 wherein the plurality of transitions are stepwise to change the diameter from a proximal end to a distal end along the longitudinal length of the small diameter, elongated probe.

75. The method of claim 40 wherein a diameter of the small diameter, elongated probe slowly tapers from a proximal end to a distal end along a longitudinal length of the small diameter, elongated probe.

76. The method of claim 40 wherein the small diameter, elongated probe has a small cross sectional profile.

77. The method of claim 40 wherein the small diameter, elongated probe vibrates in a direction transverse to at least a portion of a longitudinal length of the small diameter, elongated probe.

78. The method of claim 40 wherein the small diameter, elongated probe is for a single use on a single patient.

79. The method of claim 40 wherein the small diameter, elongated probe is disposable.

80. A method of improving the visibility of an elongated ultrasonic probe having a small diameter for destroying a biological material comprising:

providing an elongated ultrasonic probe having a longitudinal length;

engaging a material of high radiopacity at a plurality of predetermined locations on an outside surface of the longitudinal length of the elongated ultrasonic probe, the material of high radiopacity allowing a location of the elongated probe to be detected when inserted into a body during a medical procedure; and adapting the elongated ultrasonic probe such that a transverse ultrasonic vibration along the longitudinal length of the elongated ultrasonic probe produces a plurality of nodes and a plurality of anti-nodes causing a biological material destroying effect along at least a portion of the longitudinal length including the material of high radiopacity.

81. The method of claim 79 wherein the medical procedure includes an imaging procedure.

82. The method of claim 79 wherein the imaging procedure is selected from the group consisting of fluoroscopy, radiography, tomography, digital x-ray imaging, ultrasound and magnetic resonance imaging (MRI).

83. The method of claim 80 wherein the material of high radiopacity comprises tantalum.

84. The method of claim 80 wherein the material of high radiopacity comprises a tantalum alloy.

85. The method of claim 80 wherein the material of high radiopacity is selected from the group consisting of tantalum, tungsten, gold, molybdenum and alloys thereof.

86. The method of claim 80 wherein the material of high radiopacity is located at a distal end of the elongated probe.

87. The method of claim 80 wherein the material of high radiopacity engages the elongated probe by a process of butt-welding.

88. The method of claim 80 wherein the material of high radiopacity engages the elongated probe by a process of brazing.

89. The method of claim 80 wherein the material of high radiopacity engages the elongated probe by a process of shrink fitting.

90. The method of claim 80 wherein the material of high radiopacity engages the elongated probe by a process of lap welding.

91. The method of claim 80 wherein the material of high radiopacity engages the elongated probe by a process of threaded fitting.

92. The method of claim 80 wherein the material of high radiopacity engages the elongated probe by a process of twisting of materials.

93. The method of claim 80 wherein the material of high radiopacity engages the elongated probe by a mechanical connection.

94. The method of claim 80 wherein the material of high radiopacity engages the elongated probe by a metallurgical connection.

* * * * *

UNITED STATES PATENT AND TRADEMARK OFFICE
CERTIFICATE OF CORRECTION

PATENT NO. : 6,730,048 B1
DATED : May 4, 2004
INVENTOR(S) : Hare et al.

It is certified that error appears in the above-identified patent and that said Letters Patent is hereby corrected as shown below:

Title page,
Item [56], References Cited, U.S. PATENT DOCUMENTS, please add
-- 6,497,667 -- to "Miller et al." and -- 6,514,210 -- to "Ohara et al."
OTHER PUBLICATIONS, please add
-- International Search Report based on PCT/US02/41363 --

Signed and Sealed this

Twenty-seventh Day of July, 2004

JON W. DUDAS
*Acting Director of the United States Patent and Trademark Office*